United States Patent [19]

Woodson

[11] Patent Number: 4,481,310

[45] Date of Patent: * Nov. 6, 1984

[54] FURFURYL ESTERS AND RESINS

[75] Inventor: Wayne D. Woodson, Danville, Ill.

[73] Assignee: CL Industries, Inc., Danville, Ill.

[ * ] Notice: The portion of the term of this patent subsequent to Oct. 23, 2001 has been disclaimed.

[21] Appl. No.: 503,081

[22] Filed: Jun. 14, 1983

Related U.S. Application Data

[63] Continuation of Ser. No. 306,965, Sep. 30, 1981, abandoned.

[51] Int. Cl.³ .................... C08F 32/06; B22C 11/22
[52] U.S. Cl. .................................. 523/144; 524/541; 524/549; 525/502; 549/472; 549/479
[58] Field of Search ............... 523/144; 524/541, 549; 525/502; 260/347.5

[56] References Cited

U.S. PATENT DOCUMENTS 2,628,249  2/1953  Bruno .............................. 260/347.5

Primary Examiner—Lewis T. Jacobs
Attorney, Agent, or Firm—Maky, Renner, Otto & Boisselle

[57] ABSTRACT

Acid-curable, condensation-type resins, particularly phenolic resin prepolymers and urea-formaldehyde and/or furfuryl alcohol-formaldehyde modified phenolic resin prepolymers, have improved properties when admixed with a dibasic acid di-ester of the composition $$R^1O_2C(CH_2)_nCO_2R^2$$

where n is from 1 to 8, $R^1$ is furfuryl, and $R^2$ is furfuryl or methyl. The di-esters are preferably added in the amount of 5–35%, by weight of total composition. These compositions are particularly useful in the preparation of sand cores and molds for foundry use which have improved strength and hardness.

The dibasic acid di-esters of the composition $$R^1O_2C(CH_2)_nCO_2R^2$$

where n is from 1 to 8, $R^1$ is furfuryl, and $R^2$ is furfuryl or methyl are not reported in the literature and are novel compounds. These di-esters are oily liquids having high boiling points and are particulary useful as resin modifiers, diluents and plasticizers. These di-esters are produced by the sodium-catalyzed transesterification reaction of furfuryl alcohol with the liquid dimethyl esters of the $C_3$–$C_{10}$ linear aliphatic dibasic acids at temperatures of about 214°–240° F.

11 Claims, No Drawings

FURFURYL ESTERS AND RESINS

This application is a continuation of application Ser. No. 306,965, filed Sept. 30, 1981 now abandoned.

BACKGROUND OF THE INVENTION

1. Field of the Invention

This invention relates to new and useful acid-curing resin compositions for use in the formation of sand cores and molds for foundry operations and to new di-esters of lower aliphatic dibasic acids.

2. Description of the Prior Art

In the foundry industry, sand is coated with resin binders and formed into molds and cores for the production of precision castings. A wide variety of techniques have been developed for the manufacture of sand cores and molds. These involve the hot box technique for mold and core formation; the shell method; the "No-Bake", and the cold-box technique.

In the hot box and shell methods, sand molds and cores are formed by heating a mixture of sand and a thermosetting resin at a temperature of about 300°–600° F. in contact with patterns which produce the desired shape for the mold or core. The resin is polymerized and a core or mold is formed. Procedures of this type are described in Dunn U.S. Pat. No. 3,059,297 and Brown U.S. Pat. No. 3,020,609.

A particular disadvantage of the hot box and shell methods is the necessity for heating the pattern boxes to 300°–600° F. to polymerize and cure the resin binder. This involves considerable expense and is generally a high cost technique.

The cold box techniques for core and mold formation involve the use of sand mixed or coated with resins which may be cured at room temperature by acid or base catalysis. Acidic or basic catalysts have been used in liquid, solid or gaseous form. Typical cold box processes are shown in Blaies U.S. Pat. No. 3,008,205; Dunn U.S. Pat. No. 3,059,297; Peters U.S. Pat. No. 3,108,340; Kottke U.S. Pat. No. 3,145,438; Brown U.S. Pat. No. 3,184,814; Robins U.S. Pat. No. 3,639,654; Australian Pat. No. 453,160 and British Pat. No. 1,225,984. Many of these processes involve the use of sulfur-containing acid catalysts such as benzene sulfonic acid, toluene sulfonic acid and the like. Richard U.S. Pat. No. 3,879,339 discloses coating sand with an organic peroxide and resin, forming into a mold or core and gassing with sulfur dioxide.

A number of U.S. and foreign patents disclose the use of furfuryl alcohol and other furfuryl-substituted compounds in resin polymerization and also the use of dibasic acids and some esters in resin compositions.

Bradley U.S. Pat. No. 2,238,030 discloses the use of di-alkenyl esters of dibasic acids in the copolymerization of addition polymers.

Dannenberg U.S. Pat. No. 2,650,211 discloses polymers including dibasic acids as precursors.

Treat U.S. Pat. No. 2,999,829 discloses the copolymerization of furfuryl alcohol and maleic anhydride in the prepatatio of foundry cores.

Case U.S. Pat. No. 3,312,650 resins bases on phenol and furfuryl alcohol modified with formaldehyde and treated with an acid catalyst.

Kirkpatrick U.S. Pat. No. 3,244,770 discloses the use of di-esters of dibasic acids in phenolic resin compositions.

Bean U.S. Pat. No. 3,248,276 discloses the use of dibasic acids in resin compositions containing condensation-type resins.

Guyer U.S. Pat. No.3,404,118 discloses the use of furfuryl glycidyl ether in molding resins.

Fitko U.S. Pat. No. 3,600,290 discloses the use of unsaturated esters in resin compositions.

Adkins U.S. Pat. No. 3,725,333 discloses the preparation of foundry molds, etc. using phenolic resins modified with furfuryl alcohol.

Laitar U.S. Pat. No. 4,051,301 discloses resins for sand cores or molds by incorporating furan into a furfuryl alcohol-modifed phenolic resin prepolymer.

Anderson U.S. Pat. No. 4,083,817 discloses the acid curing of mixtures of furan-formaldehyde resins with phenolic resins for production of foundry cores and molds.

British Pat. Nos. 626,763 and 992,345 disclose the use of glyceryl esters and other esters of aliphatic dibasic acids in condensation polymers.

The bis(tetrahydrofurfuryl) ester of adipic acid is known but does not undergo condensation type polymerization.

The above noted patents, however, do not consider the problem of the preferential polymerization of furfuryl alcohol when admixed with phenolic and other condensation-type resins and the problem of short bench life, or any way to overcome these problems.

SUMMARY OF THE INVENTION

It is one object of the invention to provide a solution to some of the aformentioned problems and provide resins having a more useful bench life and produce cores and molds having greater strength and hardness.

Another object of the invention is to provide resin compositions having the properties and desires characteristics of furfuryl alcohol-containing resins without the problems of short bench life and working time.

Another object of the invention is to provide a novel class of compounds which is useful in modifying condensation-type resins.

Other objects of the invention will become apparent from time to time throughout the specification and claims as hereinafter related.

The above stated objects and other apparent objects of the invention ase accomplished by novel resin compositions comprising acid-curable, condensation-type resins, particularly phenolic resin prepolymers and urea-formaldehyde and/or furfuryl alcohol formaldehyde modified phenolic resin prepolymers admixed with a dibasic acid di-ester of the composition

where n is from 1 to 8, $R^1$ is furfuryl, and $R^2$ is furfuryl or methyl. The di-esters are preferably added in the amount of 5–35%, by weight of total composition. These compositions are particularly useful in the preparation of sand cores and molds for foundry use which have improved strength and hardness.

The dibasic acid di-esters of the composition

where n is from 1 to 8, $R^1$ is furfuryl, and $R^2$ is furfuryl or methyl are not reported in the literature and are novel compounds. These di-esters are oily liquids having high boiling points and are particularly useful as resin modifiers, diluents and plasticizers. These di-esters are produced by the sodium-catalyzed transesterification reaction of furfuryl alcohol with the liquid dimethyl esters of the $C_3$–$C_{10}$ linear aliphatic dibasic acids at temperatures of about 214°–240° F.

DESCRIPTION OF THE PREFERRED EMBODIMENTS

As noted above, the use of furfuryl alcohol modified resins is well reported in the prior art. The prior art, however, does not treat the problem of preferential polymerization of furfuryl alcohol when admixed with phenolic and other resins or suggest any solution to the problem. In this invention, it has been discovered that a novel class of esters, viz. the furfuryl-methyl esters or the difurfuryl esters of $C_3$–$C_{10}$ linear aliphatic dibasic acids may be mixed with phenolic resin prepolymers (and other condensation-type resins) and copolymerized by acid catalysis uniformly. The use of these resin compositions in the preparation of foundry cores and molds results in easier handling of the resins and the sand-resin compositions and improved foundry cores and molds, both in tensile strength and hardness.

The preparation of the novel esters and their properties and use in resin compositions will be discussed separately below.

PREPARATION AND PROPERTIES OF FURFURYL DI-ESTERS

The difurfuryl esters and mixed methyl-furfuryl esters of aliphatic dibasic acids are prepared by a sodium-catalyzed transesterification of the corresponding dimethyl esters.

EXAMPLE I

Preparation of Difurfuryl Glutarate

Furfuryl alcohol is a moderately high boiling liquid, b.p. 340° F. Dimethyl glutarate is a very high boiling liquid, b.p. 417° F.

196 parts by wt. of furfuryl alcohol and 160 parts by wt. dimethyl glutarate (stoichiometric proportions) were mixed and 0.5–0.75% wt. sodium metal added. The mixture was heated to a temperature in the range from 214°–240° F. under a nitrogen atmoshpere. Methanol was evolved and removed as the reaction progressed. After a period of 4 hours, a waxy solid was obtained. After washing the product with water, the residure was a liquid which was identified as difurfuryl glutarate by gas chromatography and mass spectrometric analysis.

Additional runs established that the mixed methyl-furfuryl ester of glutaric acid is obtained when the reaction is not run long enough and does not go to completion. When the reaction is carrier out with a stoichiometric excess of furfuryl alcohol, e.g. 2:1 mol ratio, the reaction goes to completion sooner but the excess furfuryl alcohol must be separated from the product. It has also been found that when the reaction temperature is allowed to go too high, there is some decomposition and an appreciable amount of difurfuryl succinate is produced.

EXAMPLE II

Preparation of Difurfuryl Succinate

Furfuryl alcohol is a moderately high boiling liquid, b.p. 340° F. Dimethyl succinate is a very high boiling liquid, b.p. 385° F.

196 parts by wt. of furfuryl alcohol and 146 parts by wt. dimethyl glutarate (stoichiometric proportions) were mixed and 0.5–0.75% wt. sodium metal added. The mixture was heated to a temperature in the range from 214°–240° F. under a nitrogen atmoshpere. Methanol was evolved and removed as the reaction progressed. After a period of 4 hours, a waxy solid was obtained. After washing with water, a liquid residue was obtained which product was identified as difurfuryl succinate.

Additional runs established that the mixed methyl-furfuryl ester of succinic acid is obtained when the reaction is not run long enough and does not go to completion. It has also been found that when the reaction temperature is allowed to go too high, there is some decomposition and an appreciable amount of difurfuryl malonate is produced.

EXAMPLE III

Preparation of Difurfuryl Adipate

Furfuryl alcohol is a moderately high boiling liquid, b.p. 340° F. Dimethyl adipate is a very high boiling liquid, b.p. 235° F., at 13 mm.

196 parts by wt. of furfuryl alcohol and 174 parts by wt. dimethyl adipate (stoichiometric proportions) were mixed and 0.5–0.75% wt. sodium metal added. The mixture was heated to a temperature in the range from 214°–240° F. under a nitrogen atmoshpere. Methanol was evolved and removed as the reaction progressed. After a period of 4 hours, a waxy solid was obtained. After washing with water, a liquid residue was obtained which product was identified as difurfuryl adipate.

Additional runs established that the mixed methyl-furfuryl ester of adipic acid is obtained when the reaction is not run long enough and does not go to completion. It has also been found that when the reaction temperature is allowed to go too high, there is some decomposition and an appreciable amount of difurfuryl glutarate is produced.

EXAMPLE IV

Preparation of Difurfuryl Malonate

Furfuryl alcohol is a moderately high boiling liquid, b.p. 340° F. Dimethyl malonate is a very high boiling liquid, b.p. 361° F.

196 parts by wt. of furfuryl alcohol and 132 parts by wt. dimethyl malonate (stoichiometric proportions) are mixed and 0.5–0.75% wt. sodium metal added. The mixture is heated to a temperature in the range from 214°–240° F. under a nitrogen atmoshpere. Methanol is evolved and removed as the reaction progressed. After a period of 4 hours, a waxy solid is obtained. The liquid product obtained after washing with water is difurfuryl malonate.

The mixed methyl-furfuryl ester of malonic acid is obtained when the reaction is not run long enough and does not go to completion. When the reaction temperature is allowed to go too high, there is some decomposition which gives an unsatisfactory result.

EXAMPLE V

Preparation of Other Difurfuryl Esters

Furfuryl alcohol is a moderately high boiling liquid, b.p. 340° F. The dimethyl esters of other lower aliphatic acids are prepared by the same transesterification reaction. Dimethyl pimelate is a very high boiling liquid, b.p. 248° F. at 10 mm. Dimethyl suberate is a still higher boiling liquid, b.p. 514° F. Dimethyl azelate boils at 313° F. at 20 mm. Dimethyl sebacate boils at 144° F. at 5 mm. These esters are well known high-boiling oleagenous liquids which have had some use as synthetic lubricants.

When furfuryl alcohol and any of the above listed dimethyl esters are mixed in stoichiometric proportions and 0.5–0.75% wt. sodium metal added and the mixture heated to a temperature in the range from 214°–240° F. under a nitrogen atmoshpere, the reaction proceeds as described above for the other esters. Methanol is evolved and removed as the reaction progresses. After a period of 4 hours, a waxy solid is obtained in each case. Water washing any of these products to remove impurities leaves a liquid residue which is a difurfuryl esters of the respective acids.

The mixed methyl-furfuryl esters are obtained when the reaction is not run long enough and does not go to completion. It has also been found that when the reaction temperature is allowed to go too high, there is some decomposition and some difurfuryl esters of the lower dibasic acids are obtained.

When the reaction is carried out using mixtures of the dimethyl esters of various $C_3$–$C_{10}$ aliphatic dibasic acids in the transesterification reaction, the difurfuryl ester (or the mixed methyl-furfuryl esters) of the various acids are produced.

USES OF FURFURYL DI-ESTER/RESIN MIXTURES

The difurfuryl esters and the mixed methyl furfuryl esters of the dibasic acids described above are compatible extenders for various condensation-type resins.

PHENOLIC RESIN COMPOSITIONS WITH DIFURFURYL GLUTARATE

EXAMPLE VI

A molding resin composition was prepared by mixing 20% wt. of liquid difurfuryl glutarate with 80% wt. of a phenol formaldehyde resin prepolymer.

A foundry-grade sand was then mixed with a benzene sulfonic acid catalyst in the amount of 45% by weight of the resin composition to be added. Then, 1.25%, by weight of the sand, of 80/20 resin-ester mixture was added to the sand and catalyst and thoroughly mixed.

The resin composition-sand mixture was formed into test biscuits, simulating a foundry core or mold, and allowed to cure for 78 minutes at about 78° F.

The test biscuits have a tensile strength of 196 lbs. after 24 hrs. as compared with a tensile strength of 161 lbs. for a control produced under the same conditions using the same phenolic resin prepolymer without the difurfuryl ester. Substantially the same results are obtained using slightly greater amounts of the mixed methyl-furfuryl glutarate ester.

Other catalysts can be used in forming the test biscuits which are customarily used in curing sand cores and molds. The aromatic sulfonic acids, including benzene sulfonic acid, toluene sulfonic acid, xylene sulfonic acid, and mixtures thereof, either alone or diluted with water and/or methanol or other diluents. Sometimes fluoboric acid or sulfuric acid may be added.

EXAMPLE VII

A molding resin composition is prepared by mixing 35% wt. of liquid difurfuryl glutarate with 65% wt. of a phenol formaldehyde resin prepolymer.

A foundry-grade sand is then mixed with a benzene sulfonic acid catalyst in the amount of 45% by weight of the resin composition to be added. Then, 1.25%, by weight of the sand, of 65/35 resin-ester mixture is added to the sand and catalyst and thoroughly mixed.

The resin composition-sand mixture is formed into test biscuits, simulating a foundry core or mold, and allowed to cure for 80 minutes at about 76° F.

The test biscuits have a tensile strengths after 24 hrs. which are better than the tensile strength of a control produced under the same conditions using the same phenolic resin prepolymer without the difurfuryl ester. The tensile strength is somewhat less than in Example VI but is substantially better than the control. Substantially the same results are obtained using slightly greater amounts of the mixed methyl-furfuryl glutarate ester.

When larger amounts of the ester are used, e.g. 40% and higher, the test results are poorer than the controls. Likewise, when lesser proportions of the ester are used, down to 5%, results are obtained which are better than the controls. While the range of 5–35% of the difurfuryl esters is preferred, a much wider range may be used where the desired function is that of a diluent or plasticizer in the ester/resin composition.

Other catalysts can be used in forming the test biscuits which are customarily used in curing sand cores and molds. The aromatic sulfonic acids, including benzene sulfonic acid, toluene sulfonic acid, xylene sulfonic acid, and mixtures thereof, either alone or diluted with water and/or methanol or other diluents. Sometimes fluoboric acid or sulfuric acid may be added.

MODIFIED RESIN COMPOSITIONS

EXAMPLE VIII

A molding resin composition is prepared by mixing 25% wt. of liquid difurfuryl glutarate with 75% wt. of a furan modified phenol formaldehyde resin prepolymer.

A foundry-grade sand is then mixed with a toluene sulfonic acid catalyst in the amount of 45% by weight of the resin composition to be added. Then, 1.25%, by weight of the sand, of 75/25 resin-ester mixture is added to the sand and catalyst and thoroughly mixed.

The resin composition-sand mixture is formed into test biscuits, simulating a foundry core or mold, and allowed to cure for 85 minutes at about 75° F.

The test biscuits have a tensile strengths after 24 hrs. which are better than the tensile strength of a control produced under the same conditions using the same furan modified phenolic resin prepolymer without the difurfuryl ester. The tensile strength is somewhat less than in Example VI but is substantially better than the control. Substantially the same results are obtained using slightly greater amounts of the mixed methyl-furfuryl glutarate ester.

Other catalysts can be used in forming the test biscuits which are customarily used in curing sand cores and molds, as noted in Examples VI and VII.

SULFUR DIOXIDE CURING OF RESINS CONTAINING ESTERS

EXAMPLE IX

A molding resin composition was prepared by mixing 20% wt. of liquid difurfuryl glutarate with 80% wt. of a phenol formaldehyde resin prepolymer.

A foundry-grade sand is then mixed with about 0.5% methyl ethyl ketone peroxide as a catalyst precursor. Then, 1.25%, by weight of the sand, of 80/20 resin-ester mixture is added to the sand and peroxide and thoroughly mixed.

The resin composition-sand mixture is formed into test biscuits, simulating a foundry core or mold, and gassed with sulfur dioxide for about 0.5-5 seconds at a temperature of from room temperature to 85°-90° F.

The test biscuits have a tensile strengths after 24 hrs. which are better than the tensile strength of a control produced under the same conditions using the same phenolic resin prepolymer without the difurfuryl ester, and also better than a furan modified phenolic resin having about the same furfuryl content.

SULFUR DIOXIDE CURING MODIFIED RESIN

EXAMPLE X

A molding resin composition was prepared by mixing 20% wt. of liquid difurfuryl glutarate with 80% wt. of a urea-formaldehyde/furan-modified phenol formaldehyde resin prepolymer.

A foundry-grade sand is then mixed with about 0.6% methyl ethyl ketone peroxide as a catalyst precursor. Then, 1.25%, by weight of the sand, of 80/20 resin-ester mixture is added to the sand and peroxide and thoroughly mixed.

The resin composition-sand mixture is formed into test biscuits, simulating a foundry core or mold, and gassed with sulfur dioxide for about 0.5-5 seconds at a temperature of 80°-85° F.

The test biscuits have a tensile strengths after 24 hrs. which are better than the tensile strength of a control produced under the same conditions using the same resin prepolymer without the difurfuryl ester.

EXAMPLE XI

A molding resin composition was prepared by mixing 20% wt. of liquid difurfuryl glutarate with 80% wt. of a phenol formaldehyde resin prepolymer.

A foundry-grade sand was then mixed with a benzene sulfonic acid catalyst in the amount of 45% by weight of the resin composition to be added. Then, 1.25%, by weight of the sand, of 80/20 resin-ester mixture was added to the sand and catalyst and thoroughly mixed.

The resin composition-sand mixture was formed into test biscuits, simulating a foundry core or mold, and allowed to cure for 78 minuts at about 78° F.

The test biscuits have a tensile strength of 196 lbs. after 24 hrs. as compared with a tensile strength of 161 lbs. for a control produced under the same conditions using the same phenolic resin prepolymer without the difurfuryl ester. Substantially the same results are obtained using slightly greater amounts of the mixed methyl-furfuryl glutarate ester.

Other catalysts may be used with this resin composition, particularly those discussed in Examples VI and VII, above.

RESINS CONTAINING DIFURFURYL ADIPATE

EXAMPLE XII

A molding resin composition is prepared by mixing 30% wt. of liquid difurfuryl adipate with 70% wt. of a phenol formaldehyde resin prepolymer.

A foundry-grade sand is then mixed with a benzene sulfonic acid catalyst in the amount of 45% by weight of the resin composition to be added. Then, 1.25%, by weight of the sand, of 70/30 resin-ester mixture is added to the sand and catalyst and thoroughly mixed.

The resin composition-sand mixture is formed into test biscuits, simulating a foundry core or mold, and allowed to cure for 80 minutes at about 76° F.

The test biscuits have a tensile strengths after 24 hrs. which are better than the tensile strength of a control produced under the same conditions using the same phenolic resin prepolymer without the difurfuryl ester. Substantially the same results are obtained using slightly greater amounts of the mixed methyl-furfuryl adipate ester.

Other catalysts may be used with this resin composition, particularly those discussed in Examples VI and VII, above.

RESINS CONTAINING DIFURFURYL SUCCINATE

EXAMPLE XIII

A molding resin composition is prepared by mixing 20% wt. of liquid difurfuryl succinate with 80% wt. of a phenol formaldehyde resin prepolymer.

A foundry-grade sand is then mixed with a benzene sulfonic acid catalyst in the amount of 45% by weight of the resin composition to be added. Then, 1.25%, by weight of the sand, of 80/20 resin-ester mixture is added to the sand and catalyst and thoroughly mixed.

The resin composition-sand mixture is formed into test biscuits, simulating a foundry core or mold, and allowed to cure for 72 minutes at about 79° F.

The test biscuits have a tensile strengths after 24 hrs. which are better than the tensile strength of a control produced under the same conditions using the same phenolic resin prepolymer without the difurfuryl ester. Substantially the same results are obtained using slightly greater amounts of the mixed methyl-furfuryl succinate ester.

Other catalysts may be used with this resin composition, particularly those discussed in Examples VI and VII, above.

RESINS CONTAINING MIXED DIFURFURYL ESTERS

EXAMPLE XIV

A molding resin composition was prepared by mixing 20% wt. of liquid difurfuryl esters of a mixture of glutaric, succinic and adipic acids with 80% wt. of a phenol formaldehyde resin prepolymer.

A foundry-grade sand was then mixed with a benzene sufonic acid catalyst in the amount of 45% by weight of the resin composition to be added. Then, 1.25%, by weight of the sand, of 80/20 resin-ester mixture was added to the sand and catalyst and thoroughly mixed.

The resin composition-sand mixture was formed into test biscuits, simulating a foundry core or mold, and allowed to cure for 80 minutes at about 75° F.

The test biscuits have a tensile strengths after 24 hrs. which are better than the tensile strength of a control produced under the same conditions using the same phenolic resin prepolymer without the difurfuryl esters. Substantially the same results are obtained using slightly greater amounts of the mixed methyl-furfuryl mixed acid esters.

Other catalysts may be used with this resin composition, particularly those discussed in Examples VI and VII, above.

RESINS CONTAINING DIFURFURYL MALONATE

EXAMPLE XV

A molding resin composition Is prepared by mixing 25% wt. of liquid difurfuryl malonate with 75% wt. of a phenol formaldehyde resin prepolymer.

A foundry-grade sand is then mixed with a benzene sulfonic acid catalyst in the amount of 45% by weight of the resin composition to be added. Then, 1.25%, by weight of the sand, of 75/25 resin-ester mixture is added to the sand and catalyst and thoroughly mixed.

The resin composition-sand mixture is formed into test biscuits, simulating a foundry core or mold, and allowed to cure for 74 minutes at about 78° F.

The test biscuits have a tensile strengths after 24 hrs. which are better than the tensile strength of a control produced under the same conditions using the same phenolic resin prepolymer without the difurfuryl ester. Substantially the same results are obtained using slightly greater amounts of the mixed methyl-furfuryl malonate ester.

Other catalysts may be used with this resin composition, particularly those discussed in Examples VI and VII, above.

RESINS CONTAINING DIFURFURYL PIMELATE

EXAMPLE XVI

A molding resin composition is prepared by mixing 15% wt. of liquid difurfuryl pimelate with 85% wt. of a phenol formaldehyde resin prepolymer.

A foundry-grade sand is then mixed with a benzene sulfonic acid catalyst in the amount of 45% by weight of the resin composition to be added. Then, 1.25%, by weight of the sand, of 85/15 resin-ester mixture is added to the sand and catalyst and thoroughly mixed.

The resin composition-sand mixture is formed into test biscuits, simulating a foundry core or mold, and allowed to cure for 74 minutes at about 80° F.

The test biscuits have a tensile strengths after 24 hrs. which are better than the tensile strength of a control produced under the same conditions using the same phenolic resin prepolymer without the difurfuryl ester. Substantially the same results are obtained using slightly greater amounts of the mixed methyl-furfuryl pimelate ester.

Other catalysts may be used with this resin composition, particularly those discussed in Examples VI and VII, above.

RESINS CONTAINING DIFURFURYL SUBERATE

EXAMPLE XVII

A molding resin composition is prepared by mixing 20% wt. of liquid difurfuryl suberate with 80% wt. of a phenol formaldehyde resin prepolymer.

A foundry-grade sand is then mixed with a benzene sulfonic acid catalyst in the amount of 45% by weight of the resin composition to be added. Then, 1.25%, by weight of the sand, of 80/20 resin-ester mixture is added to the sand and catalyst and thoroughly mixed.

The resin composition-sand mixture is formed into test biscuits, simulating a foundry core or mold, and allowed to cure for 70 minutes at about 82° F.

The test biscuits have a tensile strengths after 24 hrs. which are better than the tensile strength of a control produced under the same conditions using the same phenolic resin prepolymer without the difurfuryl ester. Substantially the same results are obtained using slightly greater amounts of the mixed methyl-furfuryl suberate ester.

Other catalysts may be used with this resin composition, particularly those discussed in Examples VI and VII, above,

RESINS CONTAININE DIFURFURYL AZELATE

EXAMPLE XVIII

A molding resin composition is prepared by mixing 35% wt. of liquid difurfuryl azelate with 65% wt. of a phenol formaldehyde resin prepolymer.

A foundry-grade sand is then mixed with a benzene sulfonic acid catalyst in the amount of 45% by weight of the resin composition to be added. Then, 1.25%, by weight of the sand, of 65/36 resin-ester mixture is added to the sand and catalyst and thoroughly mixed.

The resin composition-sand mixture is formed into test biscuits, simulating a foundry core or mold, and allowed to cure for 78 minutes at about 78° F.

The test biscuits have a tensile strengths after 24 hrs. which are better than the tensile strength of a control produced under the same conditions using the same phenolic resin prepolymer without the difurfuryl ester. Substantially the same results are obtained using slightly greater amounts of the mixed methyl-furfuryl azelate ester.

Other catalyst may be used with this resin composition, particularly those discussed in Examples VI and VII, above.

RESINS CONTAINING DIFURFURYL SEBACATE

EXAMPLE XIX

A molding resin composition is prepared by mixing 20% wt. of liquid difurfuryl sebacate with 80% wt. of a phenol formaldehyde resin prepolymer.

A foundry-grade sand is then mixed with a benzene sulfonic acid catalyst in the amount of 45% by weight of the resin composition to be added. Then, 1.25%, by weight of the sand, of 80/20 resin-ester mixture is added to the sand and catalyst and thoroughly mixed.

The resin composition-sand mixture is formed into test biscuits, simulating a foundry core or mold, and allowed to cure for 78 minutes at about 78° F.

The test biscuits have a tensile strengths after 24 hrs. which are better than the tensile strength of a control produced under the same conditions using the same phenolic resin prepolymer without the difurfuryl ester. Substantially the same results are obtained using slightly greater amounts of the mixed methyl-furfuryl sebacate ester.

Other catalysts may be used with this resin composition, particularly those discussed in Examples VI and VII, above.

While this invention has been described fully and completely with special emphasis upon several preferred embodiments, it should be understood that within the scope of the appended claims this invention may be practiced otherwise than as specifically described herein.

I claim:

1. An acid curable resin binder composition for sand cores or molds comprising
    an admixture of an acid curable condensation-type resin precondensate, and
    a dibasic acid di-ester of the composition $$R^1O_2C(CH_2)_nCO_2R^2$$

where n is from 1 to 8, $R^1$ is furfuryl, and $R^2$ is furfuryl or methyl.

2. A resin binder composition according to claim 1 in which
said resin precondensate is a phenolic resin prepolymer.

3. A resin binder composition according to claim 2 in which
said resin precondensate is a phenolic resin prepolymer modified by urea-formaldehyde or furfuryl alcohol-formaldehyde or mixtures thereof.

4. A resin binder composition according to claim 1 in which
said dibasic acid di-ester is a mixture of dibasic acid di-esters in which n is a plurality of numbers from 1 to 8.

5. A resin binder composition according to claim 1 in which
said resin precondensate is present in the proportion of 65-95% wt., and
said dibasic acid diester is present in the proportion of 5-35% wt.

6. A molding composition comprising
a major amount of a particulate filler, and
a minor amount of a resin binder composition according to claim 5.

7. A molding composition according to claim 6 in which
said particulate filler is a foundry grade sand.

8. A sand core or mold produced by
forming the composition of claim 6 into a predetermined shape and polymerizing or curing said resin binder composition by treatment with acid.

9. A sand core or mold produced by
forming the composition of claim 6 into a predetermined shape and polymerizing or curing said binder composition by treatment with an aromatic hydrocarbon sulfonic acid.

10. A sand core or mold produced by
forming the composition of claim 6 into a predetermined shape and polymerizing or curing said resin binder composition by in situ formation of a strong acid therein.

11. A sand core or mold produced by
forming the composition of claim 6 into a predetermined shape and polymerizing or curing said resin binder composition by in situ formation of sulfuric acid therein.

* * * * *